(12) United States Patent
Chen (10) Patent No.: US 7,056,712 B2
(45) Date of Patent: Jun. 6, 2006

(54) TREATMENT OF GLYCOGEN STORAGE DISEASE TYPE II

(75) Inventor: Yuan-Tsong Chen, Chapel Hill, NC (US)

(73) Assignee: Duke University, Durham, NC (US)

( * ) Notice: Subject to any disclaimer, the term of this patent is extended or adjusted under 35 U.S.C. 154(b) by 596 days.

(21) Appl. No.: 09/902,461

(22) Filed: Jul. 10, 2001

(65) Prior Publication Data

US 2002/0110551 A1    Aug. 15, 2002

Related U.S. Application Data

(60) Provisional application No. 60/219,237, filed on Jul. 18, 2000.

(51) Int. Cl.
    *C12N 9/00*    (2006.01)
(52) U.S. Cl. ...................................... 435/183
(58) Field of Classification Search ................. 435/200
    See application file for complete search history.

(56) References Cited

U.S. PATENT DOCUMENTS 6,118,045 A    9/2000   Reuser et al. .................. 800/14

FOREIGN PATENT DOCUMENTS

WO    WO 00/34451    6/2000

OTHER PUBLICATIONS

Poenaru, L., Approach to Gene Therapy of Glycogenosis Type II (Pompe Disease), *Molecular Genetics and Metabolism*, 70 (3):163-169 (2000).
Hirschhorn, R., "Glycogen Storage Disease Type II: Acid α-Glucosidase (Acid Maltase) Deficiency", *The Metabolic and Molecular Bases of Inherited Disease*, (77) 11:2443-2464 (1995).
Barton, N.W., et al., "Therapeutic response to intravenous infusions of glucocerebrosidase in a patient with Gaucher disease", *Proc. Natl. Acad. Sci*, 87:1913-1916 (Mar. 1990).
Lauer, R.M., "Administration of a Mixture of Fungal Glucosidases to a Patient with Type II Glycogenosis (Pompe's Disease)", *Pediatrics*, 42:672-676 (1968).
Van den Hout., et al., "Enzyme therapy for Pompe disease with recombinant human α-glucosidase from rabbit milk", *J. Inherit. Metab. Dis.*, 24:266-274 (2001).
Williams, J.C., et al., "Enzyme Replacement in Pompe Disease With an α-Glucosidase-Low Density Lipoprotein Complex*", *Birth Defects: Original Article Series*, 16 (1):415-423 (1980).
Yang, H.W., et al., "Recombinant Human Acid α-Glucosidase Corrects Acid α-Glucosidase-Deficient Human Fibroblasts, Quail Fibroblasts, and Quail Myoblasts", *Pediatric Research*, 43 (3):374-380 (1998).

Amalfitano, A., et al., "Recombinant human acid α-glucosidase enzyme therapy for infantile glycogen storage disease type II: Results of a phase I/II clinical trial", *Genetics in Medicine*, 3 (2):132-138 (2001).
Ausems, M., et al., "Frequency of glycogen storage disease type II in The Netherlands: implications for diagnosis and genetic counselling", *European Journal of Human Genetics*, 7:713-716 (1999).
Bijvoet, A.G.A., et al., "Recombinant human acid α-glucosidase: high level production in mouse milk, biochemical characteristics, correction of enzyme deficiency in GSDII KO mice", *Human Molecular Genetics*, 7 (11):1815-1824 (1998).
Bijvoet, A.G.A., et al., "Human acid α-glucosidase from rabbit milk has therapeutic effect in mice with glycogen storage disease type II", *Human Molecular Genetics*, 8 (12):2145-2153 (1999).
Brooks, D.A., "Immune Response to Enzyme Replacement Therapy in Lysosomal Storage Disorder Patients and Animal Models", *Molecular Genetics and Metabolism*, 68:268-275 (1999).
de Barsy, T., et al., "Enzyme Replacement in Pompe Disease: An Attempt with Purified Human Acid α-Glucosidase*", *Birth Defects:Original Article Series*, 9 (2):184-190 (1973).
Fuller, M., et al., "Isolation and characterisation of a recombinant, precursor form of lysosomal acid α-glucosidase", *Eur. J. Biochem*, 234:903-909 (1995).
Hermans, M.M.P., et al., "The effect of a single base pair deletion (ΔT525) and a C1634T missense mutation (pro545leu) on the expression of lysosomal α-glucosidase in patients with glycogen storage disease type II", *Human Molecular Genetics*, 3 (12):2213-2218 (1994).
Hermans, M.M.P., et al., "The conservative substitution Asp-645→Glu in lysosomal α-glucosidase affects transport and phosphorylation of the enzyme in an adult patient with glycogen-storage disease type II", *Biochem. J.*, 289:687-693 (1993).
Hermans, M.M.P., et al., "Identification of a Point Mutation in the Human Lysosomal α-Glucosidase Gene Causing Infantile Glycogenosis Type II", *Biochemical and Biophysical Research Communications*, 179 (2):919-926 (1991).
Hoefsloot, L.H., et al., "Characterization of the human lysosomal α-glucosidase gene", *Biochem. J.*, 272:493-497 (1990).

(Continued)

*Primary Examiner*—Michael Meller
(74) *Attorney, Agent, or Firm*—Nixon & Vanderhye P.C.

(57) ABSTRACT

Methods of treating glycogen storage disease type II, by administering acid α-glucosidase, are described, as are compositions for use in treatment of glycogen storage disease type II.

21 Claims, 5 Drawing Sheets

OTHER PUBLICATIONS

Hug, G., et al., "Treatment Related Observations in Solid Tissues, Fibroblast Cultures and Amniotic Fluid Cells of Type II Glycogenosis, Hurler Disease and Metachromatice Leukodystrophy*", *Birth Defects: Original Articles Series*, 9 (2):160-183 (1973).

Kikuchi, T., et al., "Clinical and Metabolic Correction of Pompe Disease by Enzyme Therapy in Acid Maltase-deficient Quail", *J. Clin. Invest.*, 101 (4):827-833 (1998).

Martiniuk, F., et al., "Recombinant Human Acid α-Glucosidase Generated in Bacteria: Antigenic, but Enzymatically Inactive", *DNA and Cell Biology*, 11 (9):701-706 (1992).

Reuser, A.J.J., et al., "Biochemical, Immunological, and Cell Genetic Studies in Glycogenosis Type II", *Am J Hum Genet*, 30:132-143 (1978).

Slonim, A.E., et al., "Improvement of muscle function in acid maltase deficiency by high-protein therapy", *Neurology*, 33:34-38 (1983).

Van der Ploeg, A.T., et al., "Intravenous Administration of Phosphorylated Acid α-Glucosidase Leads to Uptake of Enzyme in Heart and Skeletal Muscle of Mice", *J. Clin. Invest.*, 87:513-518 (1991).

Wu, J-Y., et al., "Expression of Catalytically Active Human Multifunctional Glycogen-Debranching Enzyme and Lysosomal Acid Alpha-Glucosidase in Insect Cells", *Biochemistry and Molecular Biology International*, 39 (4):755-764 (1996).

Watson, J.G., et al., "Bone Marrow Transplantation for Glycogen Storage Disease Type II (Pompe's Disease)", *N. Engl. J. Med.*, 314:385 (1986).

Martiniuk, F., et al., "Carrier Frequency for Glycogen Storage Disease Type II in New York and Estimates of Affected Individuals Born With the Disease", *American Journal of Medical Genetics*, 76:69-72 (1998).

Schiffmann, R., et al., "Infusion of α-galactosidase A reduces tissue globotriaosylceramide storage in patients with Fabry disease", *Proc. Natl. Acad. Sci.*, 97 (1):365-370 (2000).

Van Hove, J.L.K, et al., "High-level production of recombinant human lysosomal acid α-glucosidase in Chinese hamster ovary cells which targets to heart muscle and corrects glycogen accumulation in fibroblasts from patients with Pompe disease", *Proc. Natl. Acad. Sci.*, 93:65-70 (1996).

Lei, K.J., et al., "Genetic Basis of Glycogen Storage Disease Type 1a: Prevalent Mutations at the Glucose-6-Phosphatase Locus", *Am. J. Hum. Gen.*, 57 (4):766-771 (1995).

Pauly, D.F., et al., "Complete correction of acid α-glucosidase deficiency in Pompe disease fibroblasts in vitro, and lysosomally targeted expression in neonatal rat cardic and skeletal muscle", *Gene Therapy*, 5 (4):473-480 (1998).

Chen, Y-T, et al., "Towards a molecular therapy for glycogen storage disease type II (Pompe disease)", *Mol. Medicine Today*, 6 (6):245-251 (2000).

Kakkis, E., et al., "Recombinant α-L-iduronidase replacement therapy in mucopolysaccharidosis 1: Results of a human clinical trial", *Am. J. Hum. Genet.*, 63 (4):A25 (1998).

Byrne, B.J., et al., "Reconstitution of Acid α-glucosidase activity in a mouse model of cardioskeleton myopathy, Pompe's Disease", Circulation, vol. 98 (17):I737 (1998).

TREATMENT OF GLYCOGEN STORAGE DISEASE TYPE II

RELATED APPLICATION

This application claims the benefit of U.S. Provisional Application No. 60/219,237 filed Jul. 18, 2000, the entire teachings of which are incorporated herein by reference.

BACKGROUND OF THE INVENTION

Glycogen storage disease type II (GSD-II) (also known as Pompe disease or acid maltase deficiency) is a fatal genetic muscle disorder caused by a deficiency of acid α-glucosidase (GAA), a glycogen degrading lysosomal enzyme (Hirschhorn, R., "Glycogen storage disease type II: acid α-glucosidase (acid maltase) deficiency", in Scriver, C. R. et al., (eds) *The Metabolic and Molecular Basis of Inherited disease*, 7$^{th}$ Ed., McGraw-Hill, New York, 1995, pp. 2443–2464). The deficiency results in lysosomal glycogen accumulation in almost all tissues of the body, with cardiac and skeletal muscle being the most seriously affected. The combined incidence of all forms of GSD-II is estimated to be 1:40,000, and the disease affects all groups without an ethnic predilection (Martiniuk, F. et al., *Amer. J. Med. Genet.* 79:69–72 (1998); Ausems, M. G. E. M. et al., *Eur. J. Hum. Genet.* 7:713–716 (1999)).

Clinically, GSD-II encompasses a range of phenotypes differing as to age of onset, organs involved and clinical severity, generally correlating with the residual amount of GAA activity. In its most severe presentation (infantile GSD-II, or Pompe disease, in which less than 1% of normal GAA activity is present), infants are affected by a hypertrophic cardiomyopathy, generalized muscle weakness and hypotonia secondary to massive glycogen accumulation in cardiac and skeletal muscles (for review, see Hirschhorn, supra). The disease progresses rapidly, with death from cardiac failure usually occurring by 1 year of age. Juvenile (1–10% of normal GAA activity) and adult-onset (10–40% of normal GAA activity) forms of the disease are characterized by lack of severe cardiac involvement, later age of onset, and slower progression, but eventual respiratory or limb muscle involvement results in significant morbidity and mortality for the affected individuals.

Drug treatment strategies, dietary manipulations, and bone marrow transplantation have been employed as means for treatment for GSD-II, without significant success (Hug, G. et al., *Birth Defects Org. Ser.* 9:160–183 (1967); Slonim, A. E. et al., *Neurology* 33:34 (1983); Watson, J. G. et al., *N. Engl. J. Med.* 314:385 (1986)). Early attempts at enzyme replacement were also unsuccessful (Hug, G. and Schubert, W. K., *J. Clin. Invest.* 46:1073 (1967); de Barsy, T. et al., *Birth Defects Orig. Art. Ser.* 9:84–190 (1973); Williams, J. C. and Murray, A. K., "Enzyme replacement in Pompe disease with an alpha glucosidase low-density lipoprotein complex", in Desnick, R. J. (ed), *Enzyme Therapy in Genetic Diseases*: 2, New York, Alan R. Liss 1980; pp. 415–423)). A need remains for effective treatment of GSD-II.

SUMMARY OF THE INVENTION

The present invention is drawn to methods of treating glycogen storage disease type II (infantile, juvenile or adult-onset) in an individual, by administering to the individual a therapeutically effective amount of acid α-glucosidase (e.g., less than about 15 mg enzyme per kilogram of body weight, preferably about 1–10 mg enzyme per kilogram of body weight, more preferably about 10 enzyme per kilogram of body weight or about 5 mg enzyme per kilogram of body weight), at a regular interval (e.g., monthly, bimonthly, weekly, twice weekly, daily). The acid α-glucosidase is human acid α-glucosidase, preferably recombinant human acid α-glucosidase, more preferably, precursor form of human acid α-glucosidase, and even more preferably precursor form of human acid α-glucosidase produced in Chinese hamster ovary cells. The acid α-glucosidase is administered periodically (e.g., monthly, bimonthly, weekly, twice weekly, daily). In preferred embodiments, the acid α-glucosidase is administered intravenously; intramuscularly; intrathecally; or intraventricularly.

The methods of the invention provide the first effective means to treat an individual with glycogen storage disease type II.

DETAILED DESCRIPTION OF THE INVENTION

The present invention is drawn to methods of treating glycogen storage disease type II (GSD-II) in an individual, by administering the enzyme, acid α-glucosidase (GAA) to the individual, as well as the use of the enzyme, GAA, in the manufacture of a medicament for the treatment of glycogen storage disease type II. As described herein, Applicants have successfully treated infants suffering from GSD-II by administering GAA to the infants on a regular basis; the infants demonstrated improvement of cardiac status, pulmonary function, and neurodevelopment, as well as reduction of glycogen levels in tissue.

As a result of these findings, it is now possible for the first time to treat GSD-II, including infantile, juvenile and adult-onset GSD-II. Although the results described herein discuss individuals with the most severe form of GSD-II (infantile GSD-II), it is expected that the methods will be equally effective in individuals affected by juvenile or adult-onset GSD-II, and may, in fact, be even more effective, as individuals with juvenile or adult-onset GSD-II have higher levels of residual GAA activity (1–10%, or 10–40%, respectively), and therefore are likely to be more immunologically tolerant of the administered GAA (e.g., they are generally cross-reactive immunoreactive material (CRIM)-positive for endogenous GAA, so that their immune systems do not perceive the GAA as a "foreign" protein, and they do not develop anti-GAA antibodies). The enhanced efficacy in such individuals can be seen in patient 3, who was CRIM-positive and did not develop anti-GAA antibodies, and who demonstrated a normal progression of developmental milestones, in contrast with the variable course that was seen in CRIM-negative patients 1 and 2 (who did develop anti-GAA antibodies).

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to improvement of cardiac status (e.g., increase of end-diastolic and/or end-systolic volumes, or reduction, amelioration or prevention of the progressive cardiomyopathy that is typically found in GSD-II) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In one preferred embodiment, treatment includes improvement of cardiac status, particularly in reduction or prevention of GSD-II-associated cardiomyopathy. The terms, "improve," "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of GSD-II (either infantile, juvenile or adult-onset) as the individual being treated, who is about the same age as the individual being treated (to ensure that the stages of the disease in the treated individual and the control individual(s) are comparable).

The individual being treated is an individual (fetus, child, adolescent, or adult human) having GSD-II (i.e., either infantile GSD-II, juvenile GSD-II, or adult-onset GSD-II). The individual can have residual GAA activity, or no measurable activity. For example, the individual having GSD-II can have GAA activity that is less than about 1% of normal GAA activity (infantile GSD-II), GAA activity that is about 1–10% of normal GAA activity (juvenile GSD-II), or GAA activity that is about 10–40% of normal GAA activity (adult GSD-II). The individual can be CRIM-positive or CRIM-negative for endogenous GAA. In a preferred embodiment, the individual is CRIM-positive for endogenous GAA. In another preferred embodiment, the individual is an individual who has been recently diagnosed with the disease. Early treatment (treatment commencing as soon as possible after diagnosis) is important for to minimize the effects of the disease and to maximize the benefits of treatment.

In the methods of the invention, human acid α-glucosidase (GAA) is administered to the individual. The GAA is in a form that, when administered, targets tissues such as the tissues affected by the disease (e.g., heart, muscle). In one preferred embodiment, the human GAA is administered in its precursor form, as the precursor contains motifs which allow efficient receptor-mediated uptake of GAA. Alternatively, a mature form of human GAA that has been modified to contain motifs to allow efficient uptake of GAA, can be administered. In a particularly preferred embodiment, the GAA is the precursor form of recombinant human GAA.

GAA is obtainable from a variety of sources. In a particularly preferred embodiment, recombinant human acid α-glucosidase (rhGAA) has been produced in Chinese hamster ovary (CHO) cell cultures is used (see, e.g., Fuller, M. et al., *Eur. J. Biochem.* 234:903–909 (1995); Van Hove, J. L. K. et al., *Proc. Natl. Acad. Sci. USA* 93:65–70 (1996); the entire teachings of these references are incorporated herein by reference). Production of GAA in CHO cells appears to yield a product having glycosylation which allows significant and efficient uptake of GAA in the desired tissues (heart and muscle); it is assumed that the glycosylation differs from that of GAA that is produced in transgenic mouse and rabbit milk (see, e.g., Bijvoet, A. G. A. et al., *Hum. Mol. Genet.* 7:1815–1824 (1998); Bijvoet, A. G. A. et al., *Hum. Mol. Genet.* 8:2145–2153 (1999)).

The GAA has a specific enzyme activity in the range of about 1.0–3.5 μmol/min/mg protein, preferably in the range of about 2–3.5 μmol/min/mg protein. In one preferred embodiment, the GAA has a specific enzyme activity of at least about 1.0 μmol/min/mg protein; more preferably, a specific enzyme activity of at least about 2.0 μmol/min/mg protein; even more preferably, a specific enzyme activity of at least about 2.5 μmol/min/mg protein; and still more preferably, a specific enzyme activity of at least about 2.75 μmol/min/mg protein.

GAA can be administered alone, or in compositions or medicaments comprising the GAA (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The GAA can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

GAA (or composition or medicament containing GAA) is administered by an appropriate route. In one embodiment, the GAA is administered intravenously. In other embodiments, GAA is administered by direct administration to a target tissue, such as heart or muscle (e.g., intramuscular), or nervous system (e.g., direct injection into the brain; intraventricularly; intrathecally). More than one route can be used concurrently, if desired.

GAA (or composition or medicament containing GAA) can be administered alone, or in conjunction with other agents, such as antihistamines (e.g., diphenhydramine) or immunosuppressants or other immunotherapeutic agents which counteract anti-GAA antibodies. The term, "in conjunction with," indicates that the agent is administered at about the same time as the GAA (or composition containing GAA). For example, the agent can be mixed into a composition containing GAA, and thereby administered contemporaneously with the GAA; alternatively, the agent can be administered contemporaneously, without mixing (e.g., by "piggybacking" delivery of the agent on the intravenous line by which the GAA is also administered, or vice versa). In another example, the agent can be administered separately (e.g., not admixed), but within a short time frame (e.g., within 24 hours) of administration of the GAA. In one preferred embodiment, if the individual is CRIM-negative for endogenous GAA, GAA (or composition containing GAA) is administered in conjunction with an immunosuppressive or immunotherapeutic regimen designed to reduce amounts of, or prevent production of, anti-GAA antibodies. For example, a protocol similar to those used in hemophilia patients (Nilsson, I. M. et al., *N. Engl. J. Med.* 318:947–50 (1988)) can be used to reduce anti-GAA antibodies. Such a regimen can also be used in individuals who are CRIM-positive for endogenous GAA but who have, or are at risk of having, anti-GAA antibodies. In a particularly preferred embodiment, the immunosuppressive or immunotherapeutic regimen is begun prior to the first administration of GAA, in order to minimize the possibility of production of anti-GAA antibodies.

GAA (or composition or medicament containing GAA) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The amount which will be therapeutically effective in the treatment the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In a preferred embodiment, the therapeutically effective amount is less than about 15 mg enzyme/kg body weight of the individual, preferably in the range of about 1–10 mg enzyme/kg body weight, and even more preferably about 10 mg enzyme/kg body weight or about 5 mg enzyme/kg body weight. The effective dose for a particular individual can be varied (e.g., increased or decreased) over time, depending on the needs of the individual. For example, in times of physical illness or stress, or if anti-GAA antibodies become present or increase, or if disease symptoms worsen, the amount can be increased.

The therapeutically effective amount of GAA (or composition or medicament containing GAA) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, GAA is administered monthly, bimonthly; weekly; twice weekly; or daily. The administration interval for a single individual need not be a fixed interval, but can be varied over time, depending on the needs of the individual. For example, in times of physical illness or stress, if anti-GAA antibodies become present or increase, or if disease symptoms worsen, the interval between doses can be decreased.

In one preferred embodiment, a therapeutically effective amount of 10 mg enzyme/kg body weight is administered weekly. In another preferred embodiment, a therapeutically effective amount of 5 mg enzyme/kg body weight is administered twice weekly.

The invention additionally pertains to a pharmaceutical composition comprising human acid α-glucosidase, as described herein, in a container (e.g., a vial, bottle, bag for intravenous administration, syringe, etc.) with a label containing instructions for administration of the composition for treatment of glycogen storage disease type II, such as by the methods described herein.

The invention will be further and more specifically described by the following examples.

Exemplification: Phase I/II Trial of Use of Recombinant Human Acid α-glucosidase Material and Methods Patients: Inclusion criteria were infants affected with infantile GSD-II having virtually absent GAA activity (<1% of normal in skin fibroblasts and/or muscle biopsy) and less than one year of age. Exclusion criteria included severe cardiorespiratory failure at baseline and/or other medical conditions likely to decrease survival. Because of the limited life expectancy of the disease following diagnosis, no placebo control was used. Historical control data indicated that virtually all patients died before 1 year of age (Table 1).

TABLE 1

Historical control data of infantile glycogen storage disease, type II

|  | Onset (months) | Death (months) | Length of disease course (months) |
|---|---|---|---|
| Duke University Medical Center (n = 30)* | | | |
| Mean ± SD | 5.1 ± 1.8 | 8.6 ± 2.4 | 3.5 ± 2.3 |
| Range | 2.4–10.3 | 3.3–12.4 | 0.0–9.0 |
| Slonim et al. (n = 10)** | | | |
| Mean ± SD | 2.5 ± 1.0 | 7.2 ± 2.8 | 4.7 ± 2.4 |
| Range | 1.0–4.0 | 4.0–12.0 | 2.0–9.0 |

*Data from Duke University Pompe Disease Registry
**Data from Slonim et al., J. Pediatr. 137:283–285 (2000).

Three infants affected with infantile GSD-II as evidenced by reduced acid α-glucosidase activity to less than 1% of normal in skin fibroblasts and/or muscle biopsy were enrolled in the study. At the protein level, both patients 1 and 2 had no detectable GAA protein while patient 3 had reduced levels of GAA protein detected by immunoblot analysis. The baseline clinical data before the initiation of the therapy are summarized in Table 2.

TABLE 2

Baseline Clinical Data on 3 Infantile Pompe Disease Patients

| Patient Number/Sex | Ethnic Background | Age rhGAA Started | Cardiac Status | Pulmonary Function | Motor Development (AIMS Score) | GAA Activity in Skin Fibroblasts (% of Normal) | CRIM* Status | Current Age |
|---|---|---|---|---|---|---|---|---|
| Patient 1/male | Caucasian | 4 months | Severe cardiomyopathy; status post cardiac arrest | Borderline normal, left main bronchus compression due to markedly enlarged heart, $O_2$ desaturation | <<$5^{th}$ % | 0.84% | Negative | 29 months |
| Patient 2/male | African-American | 3 months | Moderate cardiomyopathy | $O_2$ desaturation during crying | <$5^{th}$ % | 0.57% | Negative | 25 months |
| Patient 3/male | Caucasian | 2 ½ months | Borderline cardiomyopathy | Normal | <<$5^{th}$ % | 0.69% | Positive | 23 months |

*CRIM = cross reactive immunoreactive material

Patient 1 presented at 2 months of age with cardiac arrest during elective surgical repair of an inguinal hernia. Subsequent evaluation when he was 4 months of age demonstrated evidence of severe hypotonia, with a motor development age estimated to be equivalent to that of a 3 week old. He also had profound cardiomyopathy and severe cardiomegaly with compression of the left main bronchus resulting in partial atelectasis of the left lung, and feeding difficulties and failure to thrive. Patients 2 and 3 were prenatally diagnosed with Pompe disease; importantly, each had a previous sibling that had died of symptoms typically attributable to the infantile GSD-II. Both patients had evidence of motor delays; in addition patient 2 had feeding difficulty, failure to thrive and severe cardiomyopathy.

Basic Design: The study was designed as a Phase I/II, open-label, single-dose, safety and efficacy study of rhGAA administered twice weekly in the 3 patients with infantile Pompe disease. The study was approved by the institutional review board, and parental written informed consent was obtained.

The study consisted of an initial Screening Phase, a 13-week Treatment Phase, and a Follow-up Treatment Phase. During the Screening Phase the initial clinical status of the patients was assessed; in addition, GAA and glycogen levels were determined in skeletal muscle biopsy samples. During the Treatment Phase, patients received intravenous infusions of rhGAA (5 mg/kg) twice weekly. Patients were closely monitored for any adverse responses to the enzyme infusions, as well as for any impact the rhGAA administrations had on the clinical progression of infantile GSD-II. General clinical assessments included routine physical examinations, supplemented by complete urine, hematological, and clinical chemistry analyses (electrolytes, glucose, creatinine, BUN, $CO_2$, protein, albumin, ALT, AST, bilirubin, alkaline phosphatase, CK and isozyme, uric acid). Exhaustive neurologic and motor function evaluations included manual muscle strength testing, Denver development testing, and AIMS (Alberta Infant Motor Scale; see Piper, M. C. and Darrah, J., *Motor Assessment of the Developing Infant*, WB Sanders Company, Philadelphia, 1994). Two-dimensional, M-mode and Doppler echocardiography were used to assess left ventricular mass, wall thickness and systolic as well as diastolic functions. Additionally, a variety of pulmonary functions (crying vital capacity, trend pulse-oximetry and end tidal carbon dioxide measurement, as well as negative inspiratory force maneuver) were monitored throughout the study. At the conclusion of the 13-week treatment phase, GAA activity, glycogen levels and histopathology of muscle biopsies obtained from the quadriceps muscles of the contra-lateral thigh of the pre-treatment biopsies were determined. The muscle biopsies were taken 3 days after the rhGAA infusion.

Enzyme source: rhGAA purified from the culture medium of rhGAA secreting CHO cells (Van Hove, J. L. K. et al., *Proc. Natl. Acad. Sci. USA* 93:65–70 (1996)) was provided as a GMP-grade, sterile and colorless solution by Synpac (North Carolina), Inc., 99 Alexander Drive, Suite NW20, Research Triangle Park, N.C. 27709. rhGAA was purified primarily as the 110-kD precursor protein with specific enzyme activity of 2.77–3.02 μmol/min/mg protein.

ELISA for anti-rhGAA antibodies: The ELISA for anti-rhGAA antibodies was a standard sandwich assay performed by Phoenix International Life Sciences, Inc. (Saint-Laurent, Quebec). Briefly, microtiter plates were coated with rhGAA at 2.0 μg/ml overnight and then blocked with bovine IgG. Patient serum, diluted to 1:100 and then serially diluted at 1:2, was reacted with the rhGAA on the plate. The amount of bound antibody was detected with a horseradish peroxidase conjugated goat anti-human secondary antibody and tetramethylbenzidine substrate by measuring the absorbances at 450 nm. Positive samples were defined as having an absorbance that was higher than the negative cutoff. This was defined as twice the A450 value of the normal human serum negative control. Titer was defined as the dilution of the serum that still had an A450 reading above the negative cutoff value.

GAA activity, glycogen content and Western blot analysis: GAA activity was assessed by measurement of 4-methyl-umbelliferyl-α-D-glucoside cleavage at pH 4.3 as previously described (Reuser, A. J. J. et al., *Am. J. Hum. Genet.* 30:132–143 (1978)). As an internal standard, acid-β-galactosidase activity was similarly assayed with the 4-methyl-umbilliferyl derivative as the substrate (Wenger, D. A. and Williams, C., "Screening for lysosomal disorders" in Hommes, F. A. (ed.), *Techniques in diagnostic human biochemical genetics: a laboratory manual*, Wiley-Liss, New York, 1991, pp. 587–617). Glycogen content was determined by treatment of tissue extracts with *A. niger* amyloglucosidase and measurement of glucose released (Van Hove, J. L. K. et al., *Proc. Natl. Acad. Sci. USA* 93:65–70 (1996)). Western blot analysis was performed with antibody raised in rabbits against purified placenta GAA (Van Hove, J. L. K. et al., supra).

Histology: One specimen of muscle was mounted on a chuck with gum tragacanth and quick-frozen in isopentane cooled by liquid nitrogen. Five micron sections were obtained and stained with hematoxylin and eosin, modified Gomori trichrome, ATPase at pH 4.35 and 9.4, nicotinamide dehydrogenase tetrazolium blue reductase, and phosphorylase. A second specimen was clamped in situ and placed in 2.5% glutaraldehyde. The tissue was processed without en bloc staining with uranyl acetate in order to avoid loss of glycogen. Semithin sections (0.5 micron) were stained with toluidine blue and thin sections stained with uranyl acetate and lead citrate and mounted on a copper grid for electron microscopy.

Results

Patient Reaction to Treatment: The three patients with infantile Pompe disease received twice weekly intravenous infusions of rhGAA for 21–25 months. No serious allergic reactions occurred during enzyme therapy. However, three episodes of skin rash, accompanied by a mild fever and increased irritability occurred in two of the patients (patient 1 two episodes, patient 2 single episode). These symptoms resolved promptly after intravenous administration of diphenhydramine. After a second episode of skin rash, patient 1 was premedicated with oral diphenhydramine just prior to all subsequent rhGAA infusions, without further episodes. Patient 2 was similarly premedicated with oral diphenhydramine just prior to all subsequent infusions, without further episodes. Multiple hematological parameters, liver functions, renal functions, and urinalyses have all been in the normal range throughout the therapy period in all treated patients.

Figure 1A:
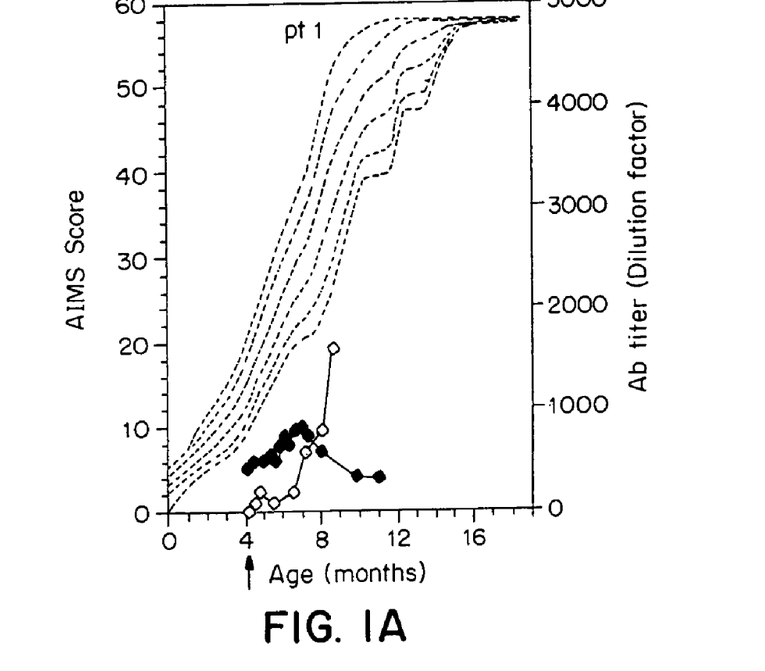
FIG. 1A–1C are a series of graphic representations depicting longitudinal data (for the first 16 months of age) on motor development as assessed by Alberta Infant Motor Scale (AIMS) (closed diamonds), and titer of antibodies to recombinant human acid α-glucosidase (rhGAA) (open diamonds) in three patients (patient 1, FIG. 1A; patient 2, FIG. 1B; patient 3, FIG. 1C) with infantile Pompe disease receiving enzyme replacement therapy. The arrow indicates when the enzyme therapy was initiated. AIMS scores in normal patients are plotted as dotted curves against age ($5^{th}$, $10^{th}$, $25^{th}$, $50^{th}$, $75^{th}$ and $95^{th}$ percentile, from bottom to top).
Figure 1B:
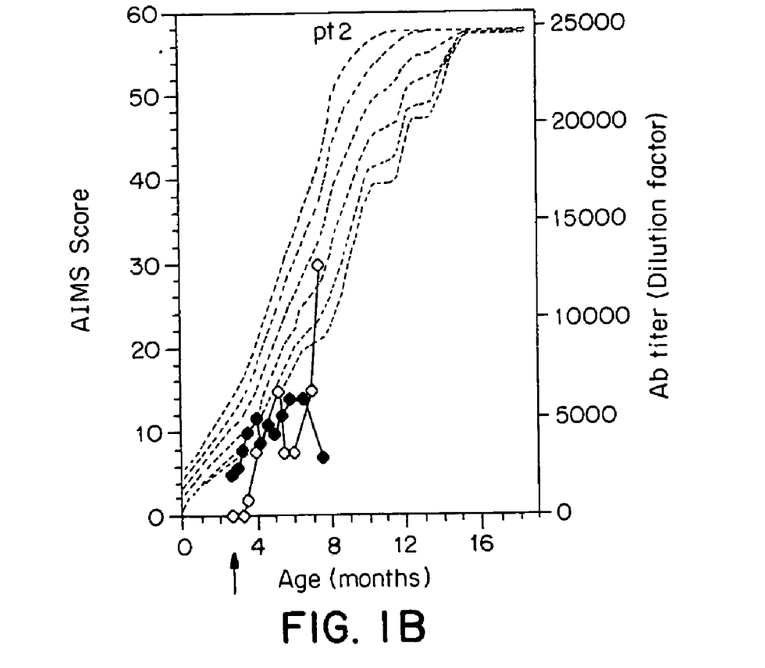
Figure 1C:
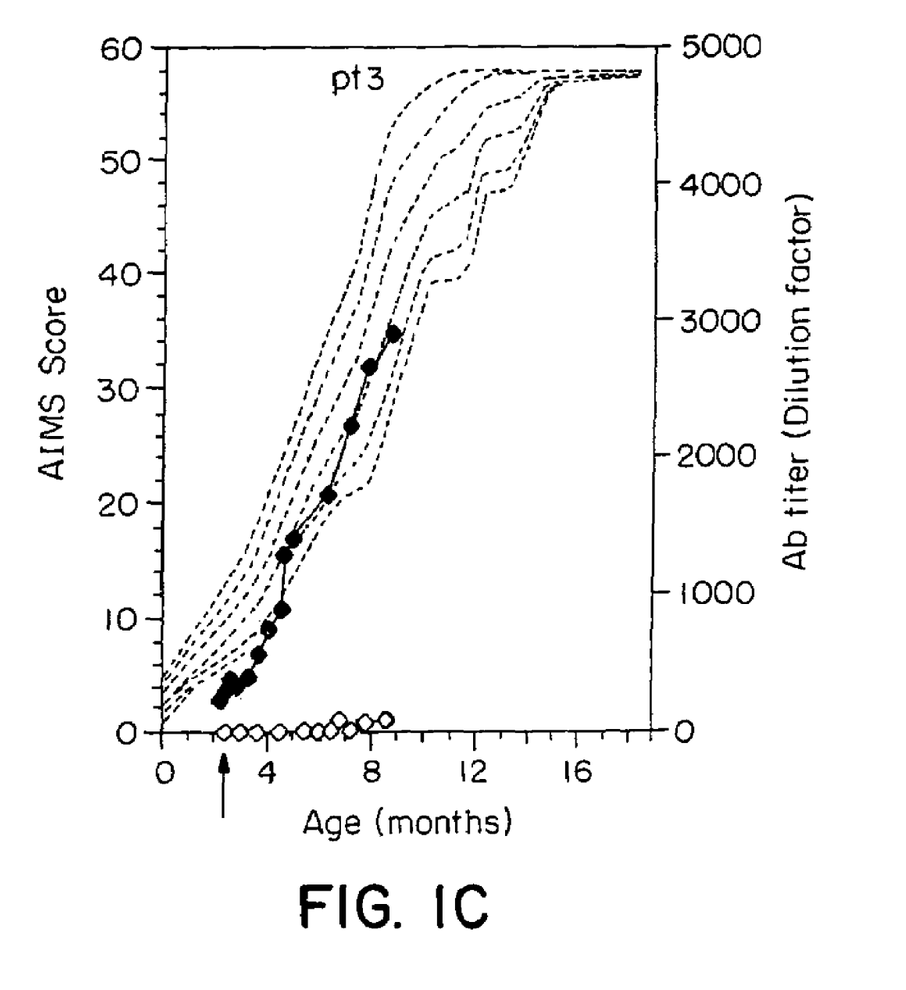

Anti-rhGAA antibodies of IgG class were detected in patients 1 and 2 as early as 3 weeks after the initiation of the enzyme therapy (FIGS. 1A–1C). Anti-rhGAA antibody titers increased to 1:1600 by week 16 in patient 1 (FIG. 1A) and 1:6400–1:12,800 between weeks 11–19 in patient 2 (FIG. 1B). As anti-rhGAA antibody titers increased, we noted that clinical improvements (noted early during therapy—see below) were no longer advancing. Neither untoward effects nor anti-rhGAA antibodies have been detected in patient 3 (FIG. 1C).

Figure 2A:
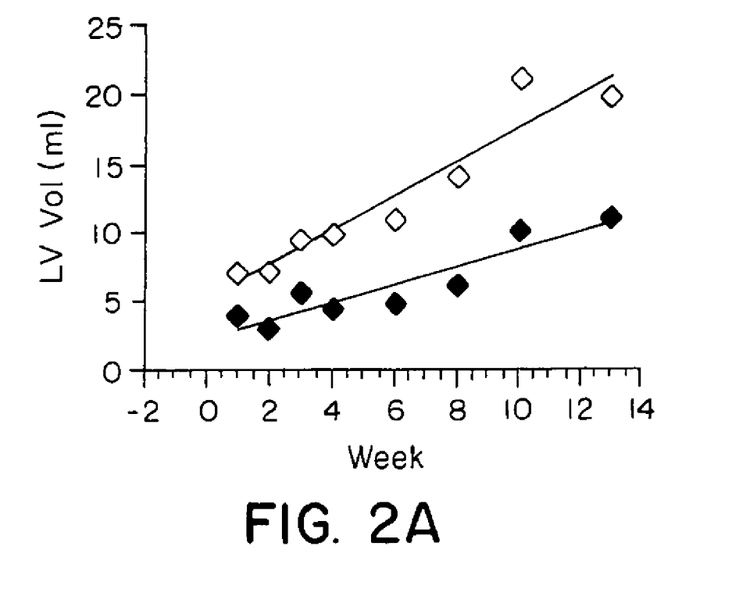
FIG. 2A–2F are a series of graphic representations depicting longitudinal two-dimensional echocardiographic measurements of left ventricular volume (FIG. 2A–2C) and mass (FIG. 2D–2F) in the three infantile Pompe disease patients receiving enzyme replacement therapy (patient 1, FIG. 2A and 2D; patient 2, FIG. 2B and 2E; patient 3, FIG. 2C and 2F). Week 0 depicts the measurements at the time of enzyme therapy initiation. Open diamonds, end-diastolic volume measurement; closed diamonds, end-systolic volume measurement.
Figure 2B:
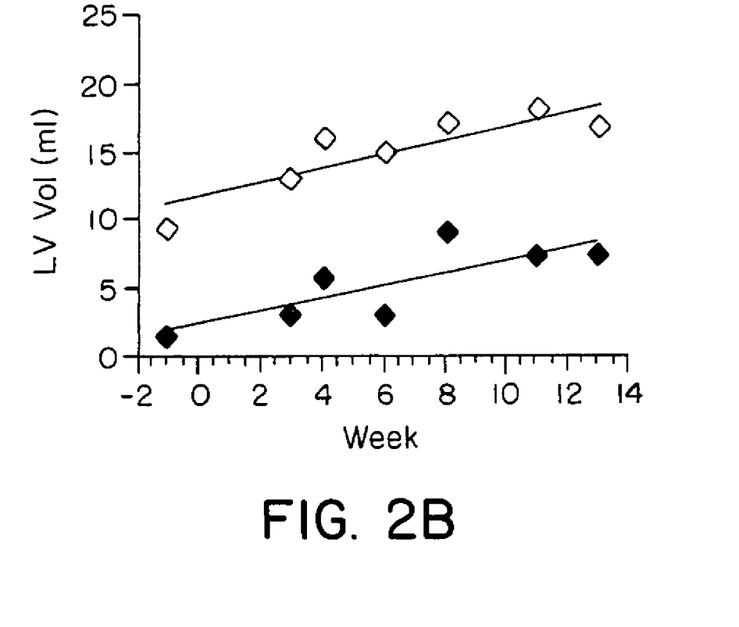
Figure 2C:
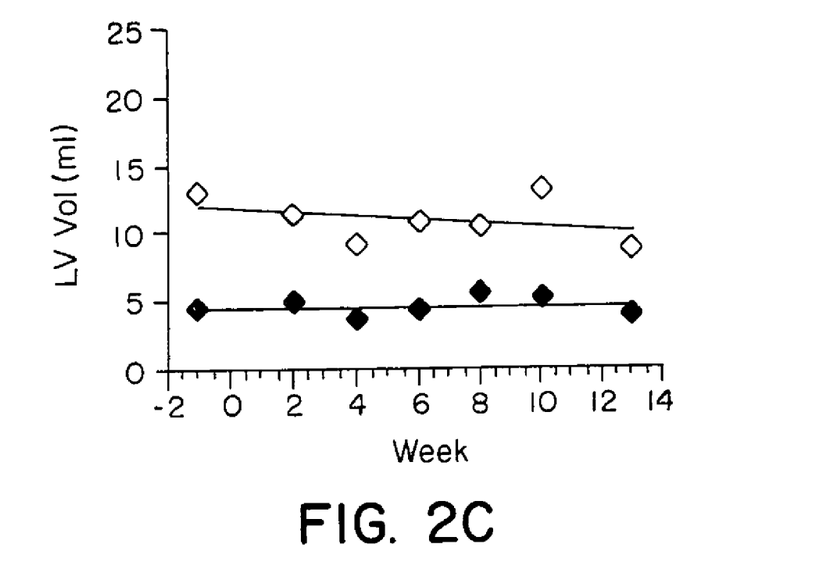
Figure 2D:
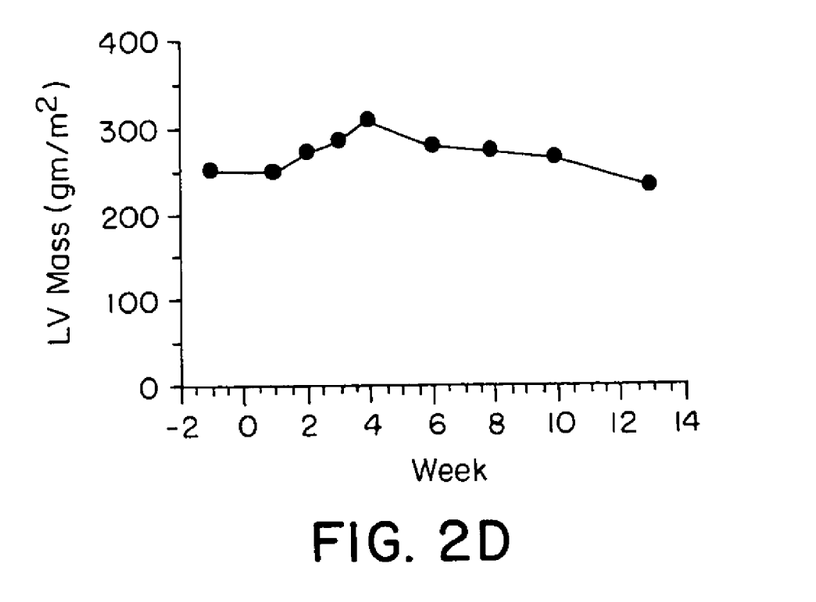
Figure 2E:
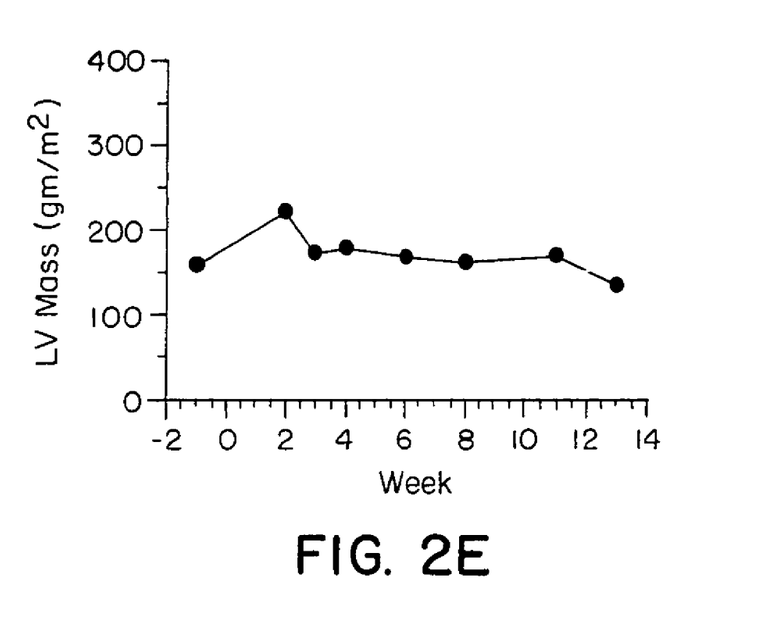
Figure 2F:
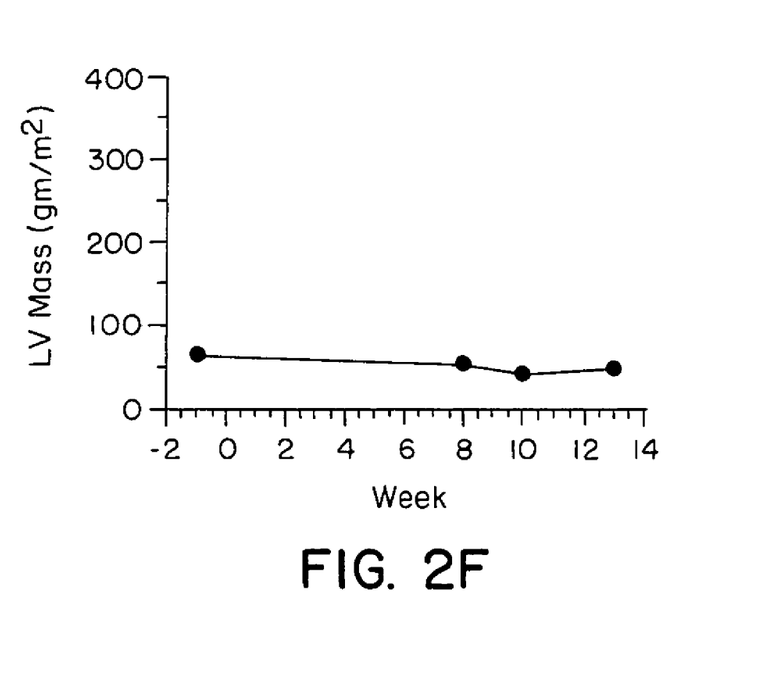

Cardiac status: Prior to the initiation of the enzyme therapy, patients 1 and 2 had severe hypertrophic cardiomyopathy associated with an increased left ventricular (LV) mass, concentric thickening of the ventricular wall and a decrease in size of the ventricular cavity (FIG. 2B, the cavity in patient 2 was almost obliterated at the end of systole). All of these features are typically seen in the untreated patient with the infantile form of Pompe disease. Additionally patient 2 was noted to have an increased LV ejection fraction (shortening fraction, 84%) reflective of a hyperdynamic shortening. None of the patients, however, had any evidence of obstruction of the ventricular outflow tract. The longitudinal echocardiographic data assessed in the patients during the first 3 months of rhGAA therapy are shown in FIG. 2A–2C. During the treatment period, in both patients 1 and 2, the LV end-diastolic and end-systolic volumes (2-D measurements) progressively increased, and up to almost 2–3 fold by the end of 3 months of therapy as compared to those measured during the pre-treatment phase (FIGS. 2A and 2B, respectively). Similar increases were noted by M-mode analysis (data not shown). The two-dimensional LV mass measurements (FIG. 2D–2F) initially increased as the LV volumes increased, but then steadily decreased during therapy, to a value that was less than the pre-treatment LV mass (reduced to 60–70% of the baseline pretreatment levels). The initial increase in mass was most likely due to an increase in the LV volume, without any changes in the LV wall thickness. These overall improvements in cardiac parameters, were sustained through the latest follow-up evaluation, although patient 1 required an intensive daily enzyme infusion for 10 days when LV mass was further increased and cardiac function compromised at the time of viral pneumonia. Otherwise the ventricular function in both patients had been normal and remained normal at the latest follow-up. Thus, the progressive cardiac morbidity normally noted in untreated infantile Pompe disease was clearly averted.

Patient 3 had a Lv mass of 64 g/$\beta^2$ (upper normal limits 65) but otherwise of normal baseline cardiac evaluation at the initiation of therapy, and has continued to be normal (with LV mass now of 33 g/$\beta^2$) since 7 months post-therapy.

Pulmonary function: In the first 2 months of therapy, improvement of pulmonary function was evident by increases in crying vital capacity (improvements of greater than 28% and 70%, in patients 1 and 2, respectively) over baseline capacities, and normalization of $O_2$ desaturation during crying ($O_2$ saturation of 70% in patient 1 and 81% in patient 2 during maximal crying). Decreased respiratory muscle strength was also evidenced in patient 1 before the therapy by a negative inspiratory force maneuver (NIFM) of −45 cm $H_2O$. With treatment, the NIFM increased to −55 cm $H_2O$. The initial improvements noted in the pulmonary functions of both patients, however, plateaued over the next 2–3 months and declined subsequently, concomitant with the rising anti-rhGAA antibodies. Both patients have subsequently become ventilator dependent after episodes of viral pneumonia precipitated respiratory insufficiency.

Patient 3 had a normal pulmonary function at initiation of therapy and has continued to demonstrate normal pulmonary function testing at the latest follow-up.

Neurodevelopment and motor assessment: Alberta Infant Motor Scale (AIMS) was used to evaluate the motor development in these infants. AIMS scores for all 3 patients started below the 5th percentile for age (FIG. 1A–1C). Patient 1 remained below the 5th percentile but showed increases within that range before beginning to decline at week 13 of the therapy (FIG. 1A). Patient 2 rose to the 25th percentile by week 5, dropped back to remain below the 5th percentile after week 7 despite increasing skills, then showed a rapid decline and loss of skills between weeks 13 and 17 (FIG. 1B). The onset of clinical declines, again was concomitant with the rising anti-rhGAA antibodies (FIG. 1A, 1B).

Concurrently administered neurologic and Denver Developmental evaluations showed in patient 1, normal personal-social, language, and fine motor developmental domains with ongoing but improving gross motor delay until week 10 when a plateau and subsequent regression became apparent. Importantly, gross motor skills had shown significant progress until week 10 but never reached normal. Patient 2 showed mild developmental delay in the gross motor sphere only with attainment of normal developmental skills in the fine motor, personal-social, and language domains until weeks 14–16 when regression occurred. Currently, both patients have normal personal-social development for age but delay in all other domains.

Patient 3 showed a steady increase of AIMS score, rising over the $10^{th}$ percentile by week 11 of the therapy and rising above the $25^{th}$ percentile by week 20 (FIG. 1C), and $90^{th}$ percentile at latest follow-up. At age 9 months, he maintained independent sitting, belly crawled reciprocally for mobility, and maintained standing with hands held. Remarkably, he has been walking independently since 12 months of age and has been able to move between squatting and standing without hand use since 14 months of age. He currently also has normal for age neurologic and Denver development evaluations in all domains.

Muscle GAA activity and glycogen content: Muscle biopsies were performed at baseline 1 week prior to the start of the rhGAA therapy except in patient 1 who had a biopsy done at the time of diagnosis which was 2 months prior to initiation of rhGAA therapy. After 4 months of rhGAA therapy, muscle biopsies were obtained from the contralateral quadriceps 3 days after the enzyme infusion (trough level). With rhGAA treatment GAA activity increased 2–3 fold over baseline pre-treatment levels in both patients 1 and 2, and 18 fold in patient 3 (Table 3).

TABLE 3

Muscle Acid α-glucosidase Activity and Glycogen Content in Infantile Pompe Disease Patients Treated with rhGAA

| | GAA Activity nmole/hr/mg Protein | Glycogen Content % Wet Weight |
|---|---|---|
| Patient 1 | | |
| Pre-therapy | 0.41 | 5.90% |
| Post-therapy | 0.95 | 7.50% |
| Patient 2 | | |
| Pre-therapy | 0.67 | 5.68% |
| Post-therapy | 1.97 | 4.43% |
| Patient 3 | | |
| Pre-therapy | 0.1 | 5.13% |
| Post-therapy | 1.84 | 1.43% |
| Control | 23.92 +/− 8.63 | 0.94 +/− 0.55% (upper normal limit; 1.5%) |

The absolute level of GAA activity approached 8% of the GAA activity seen in normal muscles. There were no appreciable changes in the muscle glycogen content in patients 1 and 2, but glycogen levels were reduced to within normal range in patient 3.

Histology: The pre-treatment biopsies of all the patients showed marked vacuolization of the muscle fibers in the frozen sections. Evaluation of the semithin sections demonstrated the fibers to be expanded by glycogen with the formation of glycogen lakes. In some fibers faint outlines of residual membranes could be discerned. Electron microscopy confirmed the presence of glycogen both in expanded lysosomes and lying free in the cytoplasm. The biopsy from patient 3 had more glycogen remaining within lysosomes than did the other two patients (data not shown).

The 4-month post-treatment biopsies of patients 1 and 2 were similar to the pre-treatment biopsies in terms of glycogen accumulation. The post-treatment biopsy of patient 3, however, had a marked decrease in visible glycogen and essentially normal histology in most of the muscle fibers. Electron microscopy showed many remaining distended lysosomes were depleted of glycogen. Some glycogen lakes and glycogen-rich lysosomes remained.

Western Blot Analysis

To investigate why anti-rhGAA antibodies developed in patients 1 and 2, but not 3, we performed a Western blot analysis specific for detection of expressed (but nonfunctional) GAA protein in fibroblasts derived from each of the patients. No GAA protein was detected in the fibroblasts of patients 1 and 2, whereas a readily detectable precursor form of GAA protein (110 kD) was found in patient 3. These patterns were previously seen in other patients with infantile GSD-II (Van der Ploeg, A. T. et al, *Am. J. Hum. Genet.* 44:787–793 (1989)). Normal fibroblasts as expected have GAA protein predominantly of 95 kD and 76 kD.

Further Studies

Three more patients have been enrolled in an additional study. All three are CRIM positive. After treatment (10 mg/kilogram body weight, weekly intravenous infusions of rhGAA) for 3–6 weeks, improvement of heart function, muscle strength, and motor development have been seen.

The teachings of all publications cited herein are incorporated herein by reference in their entirety.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method of treating glycogen storage disease type II in a human individual having glycogen storage disease type II, comprising administering to the individual a therapeutically effective amount of human acid α-glucosidase periodically at an administration interval, wherein the human acid α-glucosidase was produced in chinese hamster ovary cell cultures.

2. The method of claim 1, wherein the glycogen storage disease type II is infantile glycogen storage disease type II.

3. The method of claim 1, wherein the glycogen storage disease type II is juvenile glycogen storage disease type II.

4. The method of claim 1, wherein the glycogen storage disease type II is adult-onset glycogen storage disease type II.

5. The method of claim 1, wherein the therapeutically effective amount of human acid α-glucosidase is less than about 15 mg of acid α-glucosidase per kilogram of body weight of the individual.

6. The method of claim 5, wherein the therapeutically effective amount of human acid α-glucosidase is about 1–10 mg of acid α-glucosidase per kilogram of body weight of the individual.

7. The method of claim 5, wherein the therapeutically effective amount of human acid α-glucosidase is about 5 mg of acid α-glucosidase per kilogram of body weight of the individual.

8. The method of claim 1, wherein the human acid α-glucosidase is recombinant human acid α-glucosidase that has been produced in chinese hamster ovary cell cultures.

9. The method of claim 1, wherein the human acid α-glucosidase is a precursor of recombinant human acid α-glucosidase that has been produced in chinese hamster ovary cell cultures.

10. The method of claim 1, wherein the administration interval is monthly.

11. The method of claim 1, wherein the administration interval is bimonthly.

12. The method of claim 1, wherein the administration interval is weekly.

13. The method of claim 1, wherein the administration interval is twice weekly.

14. The method of claim 1, wherein the administration interval is daily.

15. The method of claim 1, wherein the human acid α-glucosidase is administered intravenously.

16. The method of claim 1, wherein the human acid α-glucosidase is administered intramuscularly.

17. The method of claim 1, wherein the human acid α-glucosidase is administered intrathecally or intraventricularly.

18. The method of claim 1, wherein the human acid α-glucosidase is administered in conjunction with an immunosuppressant.

19. The method of claim 18, wherein the immunosuppressant is administered prior to any administration of human acid α-glucosidase to the individual.

20. A method of treating cardiomyopathy associated with glycogen storage disease type II in an human individual having glycogen storage disease type II, comprising administering to the individual a therapeutically effective amount of human acid α-glucosidase periodically at an administration interval, wherein the human acid α-glucosidase was produced in chinese hamster ovary cell culture.

21. The method of claim 1, wherein the administration interval is varied over time.

* * * * *

(12) INTER PARTES REVIEW CERTIFICATE (1926th)
United States Patent  (10) Number: US 7,056,712 K1
Chen  (45) Certificate Issued: Feb. 19, 2021

(54) TREATMENT OF GLYCOGEN STORAGE DISEASE TYPE II

(75) Inventor: Yuan-Tsong Chen

(73) Assignee: DUKE UNIVERSITY

Trial Number:

IPR2013-00535 filed Aug. 28, 2013

Inter Partes Review Certificate for:

Patent No.: 7,056,712
Issued: Jun. 6, 2006
Appl. No.: 09/902,461
Filed: Jul. 10, 2001

The results of IPR2013-00535 are reflected in this inter partes review certificate under 35 U.S.C. 318(b).

INTER PARTES REVIEW CERTIFICATE
U.S. Patent 7,056,712 K1
Trial No. IPR2013-00535
Certificate Issued Feb. 19, 2021

AS A RESULT OF THE INTER PARTES REVIEW PROCEEDING, IT HAS BEEN DETERMINED THAT:

Claims 1-9, 11, 12, 15 and 18-21 are cancelled.

\* \* \* \* \*